United States Patent [19]

Venegas

[11] Patent Number: 5,074,297
[45] Date of Patent: Dec. 24, 1991

[54] SELF-SEALING MASK FOR DELIVERING INTERMITTENT POSITIVE PRESSURE VENTILATION

[75] Inventor: Jose G. Venegas, Nahant, Mass.

[73] Assignee: The General Hospital Corporation, Boston, Mass.

[21] Appl. No.: 453,988

[22] Filed: Dec. 19, 1989

[51] Int. Cl.$^5$ ............................................ A61M 16/00
[52] U.S. Cl. ......................... 128/204.18; 128/205.13; 128/205.25
[58] Field of Search ................ 128/204.18, 205.13, 128/205.14, 202.28, 202.29, 203.11, 205.16, 205.17, 205.25

[56] References Cited

U.S. PATENT DOCUMENTS

| | | |
|---|---|---|
| 1,610,793 | 12/1926 | Kaufman . |
| 2,130,555 | 9/1938 | Malcom . |
| 2,428,451 | 10/1947 | Emerson ........................ 128/205.13 |
| 3,045,668 | 7/1962 | Lee . |
| 4,226,234 | 10/1989 | Gunderson ...................... 128/205.24 |
| 4,498,472 | 2/1985 | Tanaka .......................... 128/205.17 |
| 4,782,832 | 11/1988 | Trimball et al. ................. 128/207.18 |
| 4,799,477 | 1/1989 | Lewis ............................. 128/206.24 |

Primary Examiner—Edgar S. Burr
Assistant Examiner—Aaron J. Lewis
Attorney, Agent, or Firm—Lahive & Cockfield

[57] ABSTRACT

A respirator mask assembly for use with intermittent positive pressure breathing treatments facilitates the formation and automatic intermittent adjustment of the seal between a patient's face and a facial unit of the respirator mask. The respirator mask assembly comprises a facial unit, an expandable piston adjacent the facial unit and a rigid support structure attached to one end of the piston, and an attachment mechanism for securing the mask assembly to a patient. During the inspiration portion of the ventilation cycle a positive pressure is developed within the mask assembly, causing the piston to expand. Because, the attachment mechanism and the support cooperate to resist significant expansion of the piston, a force is generated which presses the facial unit against the patient's face and maintains an air tight seal. When pressure within the masks unit decreases, the contact force on the facial unit is likewise decreased and the seal is eliminated.

18 Claims, 2 Drawing Sheets

SELF-SEALING MASK FOR DELIVERING INTERMITTENT POSITIVE PRESSURE VENTILATION

BACKGROUND OF THE INVENTION

This invention relates to respirator face masks, and more particularly to such face masks for use with intermittent positive pressure breathing ("IPPB") apparatuses.

Many individuals who suffer from respiratory disease or respiratory ailments require breathing assistance from mechanical ventilators. For example, patients with chronic obstructive lung disease approaching respiratory failure due to muscular fatigue could be allowed to rest their respiratory muscles by receiving intermittent positive pressure breathing (IPPB) treatment. Such patients do poorly when mechanically ventilated after tracheal intubation.

During conventional IPPB, a breathing gas is conveyed by a ventilator to a respirator face mask which is held in place over a patient's face and which communicates with a patient's airway. As pressure is increased inside the face mask during inspiration, a net force is generated on the mask which tends to separate the mask and its peripheral sealing edges from the face. Such separating force decreases the contact pressure between the mask and the skin and potentiates air leaks. To create and maintain a sufficient seal, current masks are pressed against the face by a continuous force, such as may be established by an elastic band extending around the patient's head. The force used to maintain such a seal often exceeds capillary pressure and results in the development of skin necrosis and pressure sores. A lower contact pressure, however, generally does not create a sufficient seal during inspiration, and results in unacceptable air leaks.

It would be desirable to provide a respirator face mask, for use with IPPB apparatuses, which maintains a sufficient seal with a patient's face, but does not exert an excessive, constant force which could result in skin necrosis and/or pressure sores.

Accordingly, it is an object of the invention to provide a respirator face mask which does not exert a constant, damaging force on a patient's face. It is another object of the invention to provide a respirator face mask which forms an adequate seal with a patient's face, but does not cause skin necrosis or pressure sores. A further object of the invention is to provide a respirator face mask which is self-sealing in response to positive ventilation pressure. Other objects and advantages of the invention will be apparent to one skilled in the art upon reading the following disclosure.

SUMMARY OF THE INVENTION

The present invention is directed to a self-sealing respirator face mask for use during intermittent positive pressure breathing assistance. The face mask of the invention obviates the need for using a constant force, often in excess of the patient's capillary pressure, to maintain a seal between the mask and the patient's face. Instead, the mask intermittently adjusts the seal with the patient's face in response to and proportionally to the positive pressure generated by the ventilator apparatus.

The respirator mask assembly of the invention comprises a facial unit which receives a breathing gas from a ventilator apparatus and communicates the gas to the airway of a patient. The facial unit has a peripherally extending, pliable seal element for supporting the unit against the patient's face. The interior of the facial unit may be adapted to communicate with the patient's airway through the patient's nose or mouth, or both. The facial unit is coupled to an intermittent seal mechanism which facilitates the intermittent adjustment of the seal between the facial unit and the patient's face.

In a preferred embodiment, the intermittent seal mechanism which facilitates the intermittent adjustment of a seal includes a hollow piston assembly having one end attached to and mounted forwardly of the facial unit, and a rigid support structure secured to its other end. An attachment mechanism originates at the support end and extends around the patient's head to maintain the respirator face mask in place and to assist in the formation and adjustment of the intermittent seal.

The seal between the face mask and the patient's face is increased during inspiration by the patient as positive pressure is created by a ventilator apparatus and conveyed through the piston assembly to the facial unit. As this occurs, the region within the piston assembly expands and the support structure tends to move away from the patient's face. However, the attachment mechanism prevents any major movement of the support while the region within the piston assembly continues to expand, forcing the seal element of the facial unit against the patient's face. This action thus adjusts (increases) the seal to allow the breathing gas to be transferred to the patient's airway without leakage from the interface of the patient's face and the face mask. When driving pressure is reduced, the force dissipates.

DETAILED DESCRIPTION OF THE INVENTION

Figure 1:
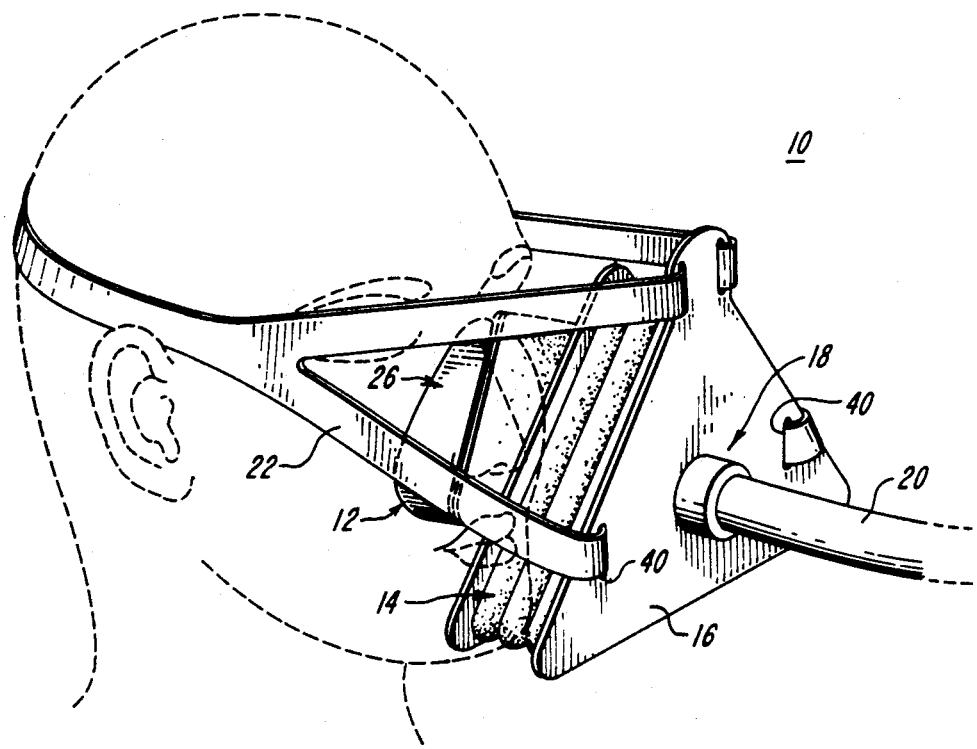
FIG. 1 is a perspective view of the respirator mask assembly of the invention having a bellows-type piston assembly in a relaxed condition.
Figure 2:
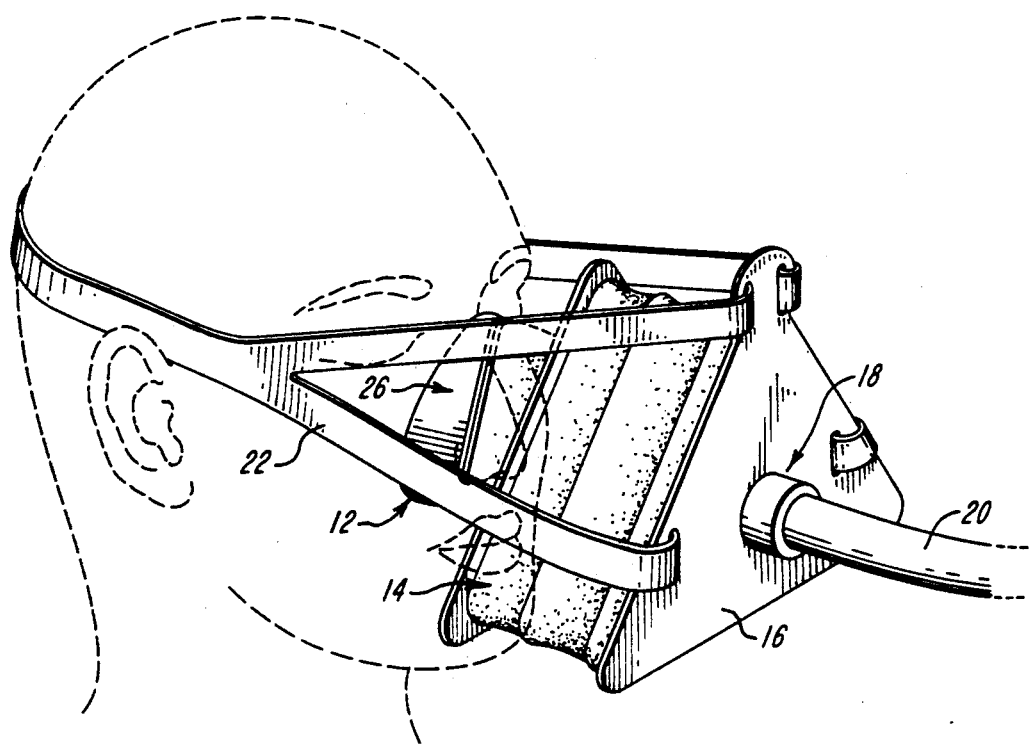
FIG. 2 is a perspective view of a respirator mask similar to that of FIG. 1 having a bellows-type piston assembly in its expanded condition.
Figure 3:
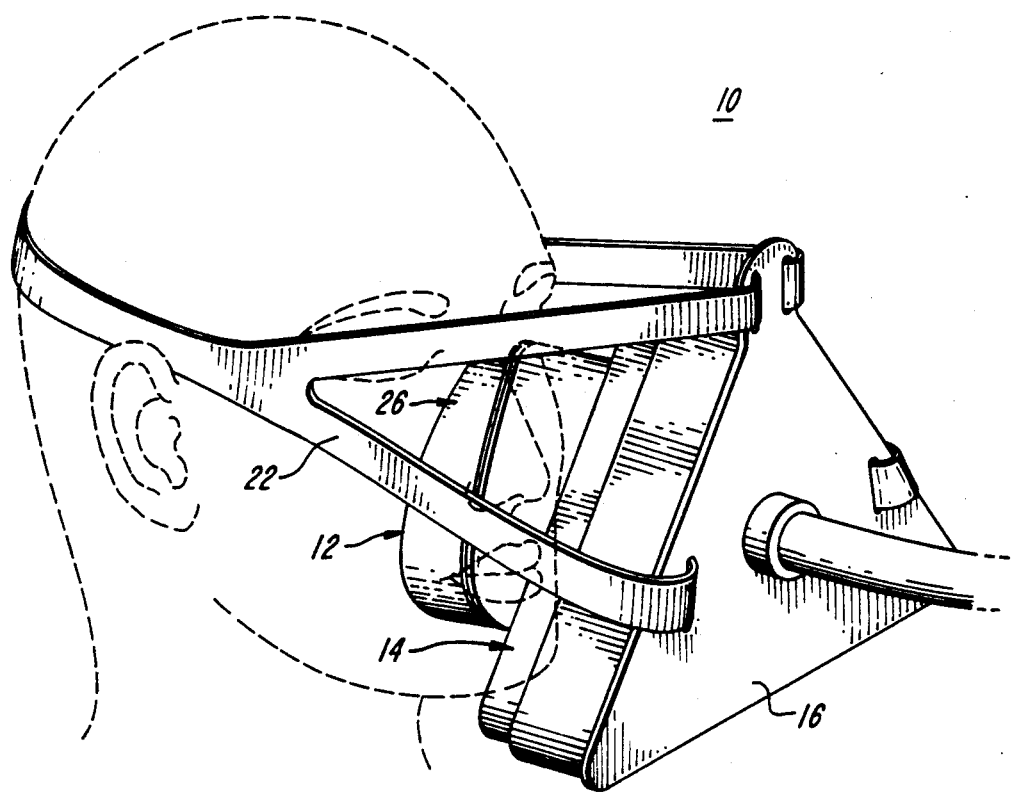
FIG. 3 is a perspective view of an alternative embodiment of the invention having a diaphragm-type piston assembly, and a face mask covering the patient's nose and mouth.

As illustrated in FIGS. 1, 2 and 3, the respirator mask assembly 10 of the present invention comprises a facial unit 12, a piston assembly 14, and a support structure 16. The mask assembly 10 also includes a port 18 extending through the support structure 16 for receiving a conduit 20 which communicates a breathing gas from a ventilator apparatus (not shown) to the facial unit 12. At least one (but preferably two) attachment strap 22 extends from the support structure 16 and around the patient's head to secure the unit 10 in place and to assist in developing an intermittent seal between the patient's face and a deformable surface established by a pliable seal element 26 of the facial unit 12.

With further reference to FIGS. 1 through 4, the facial unit 12 defines an interior region 24 for containing a breathing gas. The facial unit 12 has a deformable surface established by a pliable seal element 26 which fits against the patient's face, and side walls 28 which form a forward end 30 of the facial unit. The forwardmost portions of side walls 28 are secured to a rear end 32 of an expandable, hollow bellows-type piston assembly 14. The forward end 34 of the assembly 14 is secured to a support structure 16. Upon the outer (forward) surface 38 of the support structure 16 is mounted a port 18 which is adapted to communicate with a conduit 20 to deliver a breathing gas to the interior chamber 36 of the piston and to the interior region 24 of the facial unit.

The facial unit 12 may be constructed in a manner and of materials well known in the art. Preferably, facial unit 12 is construed of a polymeric material and is adapted to fit over a patient's nose, mouth or both, to communicate with the patient's airway. It is desirable that the facial unit 12 (as well as piston assembly 14 and support 16) have a relatively slim profile such that the patient's vision is not unduly restricted. Consequently, triangular and ovoid profiles are preferred, however other shapes may be used as well.

The piston assembly 14 may comprise virtually any apparatus or structure, the volume of which is able to expand in response to increased Pressure. In a preferred embodiment, illustrated in FIGS. 1, 2 and 4, the piston 12 is an expandable bellows. FIG. 3 illustrates another embodiment in which the piston is a low friction or frictionless diaphragm which provides good sealing properties. An exemplary diaphragm is the Bellofram Rolling Diaphragm manufactured by Bellofram Corporation. In addition to bellows and diaphragms, other piston structures may be used which have low friction, are able to expand in response to pressure, and provide good sealing properties.

The support structure 16 preferably is constructed of a material which is of sufficient rigidity that it does not deform when pressure within facial unit 12 and piston assembly 14 is increased. Preferably the support structure is manufactured of a Polymeric material and substantially corresponds in area and shape to the Piston assembly 14. Alternatively, the support structure 16 may be flexible, so long as the attachment strap 22 limits movement of the piston assembly 14. The outer surface 38 of support 16 features a port 18 which is adapted to communicate with a ventilator apparatus (not shown) through conduit 20. In addition, support structure 16 has apertures 40 or similar devices for engaging an attachment strap 22.

Attachment strap 22 may comprise one or more straps or similar members which extend from support structure 16 and around the patient's head. The strap 22 may be constructed or virtually any material (elastic or inelastic) which will maintain the assembly 10 in place and will rapidly resist the tendency of the support 16 to move away from a patient's face (forward) in response to an increase in pressure within the piston assembly 14 and facial unit 12. Preferably, the strap 22 is constructed of an inelastic material, and it is adjustable so that it can conveniently fit a variety of head sizes.

Figure 4:
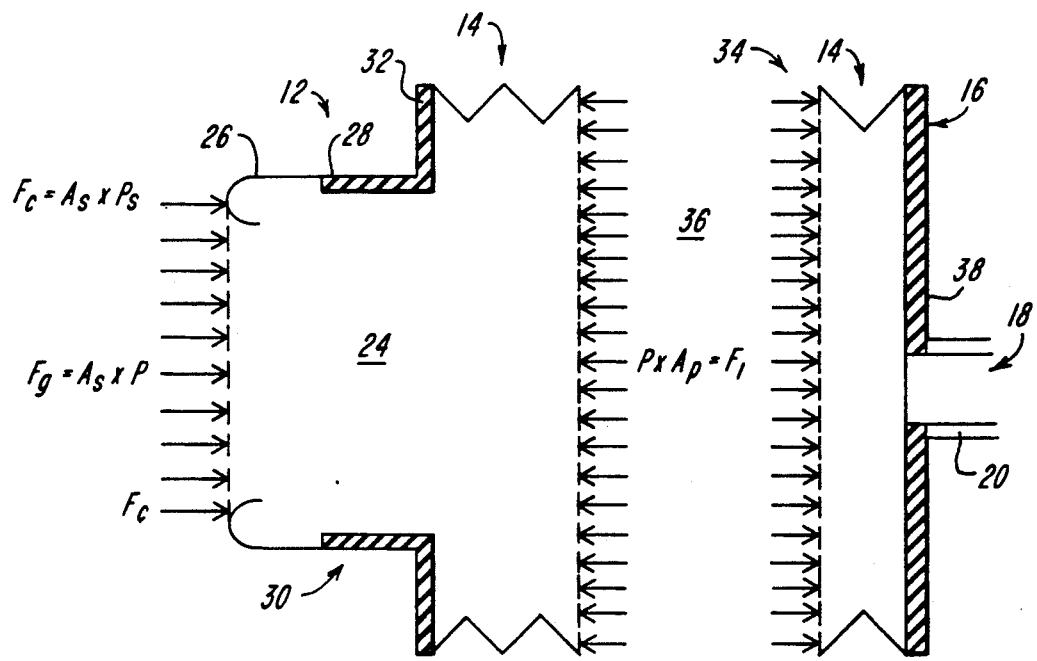
FIG. 4 is a sectional view of the respirator mask of FIG. 1.

The relationship between the piston assembly 14 and the facial unit 12 necessary to ensure the intermittent self sealing function of the respirator mask 10 in response to positive pressure is illustrated in FIG. 4. In order for the respirator mask assembly 10 to be self sealing the effective cross-sectional area ($A_p$) of piston assembly 14 must be greater than the sum of the area of the face ($A_f$) covered by facial unit 12 and the contact area ($A_s$) at the interface of the mask and the face.

As pressure (P) increases within the mask during ventilation, the piston assembly 14 is expanded generating a force $$F = P \cdot A_p.$$

This force is resisted, on one side, by the increasing tension of strap 22 (FIGS. 1-3), and on the opposite side by the facial unit 12. For static equilibrium to occur, the effective contact force ($F_c$) between the facial unit 12 and the patient's face can be calculated as $$F_c = F_O + P (A_p - A_f), \text{ and } F_c = A_s \cdot P_s$$

where $F_O$ is the initial contact force at ambient pressure and $P_s$ is the sealing contact pressure between the face and the pliable element.

Since $A_p$ is greater than $A_f$, $F_c$ increases in proportion to P. There is no need to maintain constant high contact pressure between the facial unit 12 and a patient's face since pressure is automatically increased during the positive pressure portion of the respiratory cycle. At this stage of the respiratory cycle, the difference in area between the piston cross section and the portion of the face covered by the facial unit 12, helps generate a net force which presses the facial unit 12 against the patient's face and forms an adequate pressure seal ($P_s$) which should be greater than P. Preferably, the value of $A_p - A_f$ should be about 1.2 to about 1.6 times greater than $A_s$ to generate an effective seal pressure ($P_s$) which is greater than P. During exhalation, P, and thus $P_s$, are decreased to a level below capillary pressure, and the possibility of skin necrosis or pressure sores in the contact area of the face is virtually eliminated.

In operation, the respirator mask assembly 10 is secured to a patient's head by way of one or more straps 22 which extend from the support structure 16 around the head. Before ventilation the pressure within the facial unit 12 and piston assembly 14 is at an ambient level and the contact pressure exerted by the facial unit 12 on the face is lower than the capillary pressure. During the positive pressure portion of the ventilation cycle, pressure in piston chamber 36 and space 24 increases, causing the piston 14 to expand. The piston continues to expand to a point where straps 22 and support structure 16 cooperate to resist further expansion of the piston assembly 14. At this point, the region interior to the piston assembly 14 continues to expand until the facial unit is pressed against the patient's face with sufficient force to form an airtight seal. Following the positive pressure portion of the respiratory cycle the pressure within chamber 36 and space 24 returns to an ambient level and the contact pressure of the facial unit 12 to the patient's face is likewise reduced to its original level.

The face mask unit of this invention may be used in a variety of applications. For example, it may be connected to an electro-mechanical ventilator (not shown) through part 18 and conduit 20. Alternatively, the unit 10 may be used with a manual, emergency ventilator apparatus (not shown) in which port 18 communicates with a breathing gas source generated by manually compressing a volume of air (such as a bag).

The breathing gas which may be used with the invention includes virtually all such gases typically used in respiratory therapy. Such gases may include, for example, air, oxygen-enriched air and pure oxygen.

Although particular embodiments of this invention have been described and are illustrated herein, it is recognized that modifications and variations may readily occur to those skilled in the art. Consequently, it is intended that the claims be interpreted to cover such modifications and equivalents.

What is claimed is:

1. A respirator mask assembly for delivery of intermittent positive pressure ventilation, comprising
   A. a selectively sealable facial unit defining an interior region for communicating with the airway of a patient;
   B. a support structure;
   C. sealing means for intermittently sealing said facial unit to a patient's face, said sealing means including a hollow piston having a first end and a second end, said first end being secured to said facial unit and said second end being secured to said support structure,
   wherein the interior region of said piston is in communication with said interior region of said facial unit, and said first end is displaceable with respect to said support structure in response to pressure variation in the interior of said piston;
   D. securing means affixed to said support structure for securing said mask assembly to the head of a patient; and
   E. means for introducing a breathable gas from a source other than said patient to said interior region of said facial unit.

2. A respirator mask assembly as in claim 1 wherein the effective cross-sectional area of the piston is greater than the area of the patient's face covered by the facial unit.

3. A respirator unit as in claim 2 wherein the effective cross-sectional area of the piston less the area of the patient's face covered by the facial unit is in the range of about 1.2 to about 1.6 times greater than the area of contact between the mask and the face.

4. A respirator mask assembly as in claim 3 wherein the volume of the piston increases in response to an increase in pressure in said region interior to the piston.

5. A respirator mask assembly as in claim 4 wherein said piston is a bellows.

6. A respirator mask assembly as in claim 4 wherein said piston is a deformable membrane.

7. A respirator mask assembly as in claim 4 wherein said piston is a diaphragm.

8. A respirator mask assembly as in claim 4 wherein said facial unit includes a deformable seal element extending about its periphery.

9. A respirator mask assembly as in claim 4 wherein the strap means comprises at least one adjustable strap which extends from opposed sides of the support structure.

10. A respirator mask assembly as in claim 4 wherein the means for communicating a breathable gas comprises a port, disposed on the support structure, which introduces the breathable gas from a source other than the patient to the piston and the facial unit.

11. A respirator mask assembly as in claim 10 wherein the source of breathable gas is an electro-mechanical ventilator.

12. A respirator mask assembly as in claim 10 wherein the source of breathable gas is a manual ventilator.

13. A respirator mask assembly as in claim 1 wherein the facial unit includes a peripheral edge adapted for support by a patient's face, the edge being substantially triangular in shape.

14. A respirator mask assembly as in claim 1 wherein the facial unit includes a peripheral edge adapted for support by a patient's face, said edge being substantially oval in shape.

15. A respirator mask assembly as in claim 1 wherein the facial unit communicates with the patient's nose.

16. A respirator mask assembly as in claim 1 wherein the facial unit communicates with the patient's mouth.

17. A respirator mask assembly as in claim 1 wherein the facial unit communicates with the patient's nose and mouth.

18. A respirator mask, comprising
   a selectively sealable facial unit able to introduce a breathable gas to a patient's airway;
   a sealing means for intermittently forming a seal between said facial unit and the patient's face, said sealing means including an expandable piston and a rigid support structure, said piston being secured at one end to said facial unit and at the other end to said support structure;
   strap means extending from said support structure for securing the respirator mask to a patient's head; and
   means for introducing a breathable gas from a source other than the patient to the facial unit.

* * * * *

UNITED STATES PATENT AND TRADEMARK OFFICE
CERTIFICATE OF CORRECTION

PATENT NO. : 5,074,297
DATED : December 24, 1991
INVENTOR(S) : Jose G. Venegas

It is certified that error appears in the above-identified patent and that said Letters Patent is hereby corrected as shown below:

Column 3, line 23, please replace "Pressure." with -- pressure. --.

Column 3, line 38, please replace "Polymeric" with -- polymeric --.

Column 3, line 39, please replace "Piston assembly 14." with -- piston assembly 14. --.

Column 5, line 9, please insert ":" after "comprising".

Signed and Sealed this

Eighth Day of June, 1993

Attest:

MICHAEL K. KIRK

*Attesting Officer*      *Acting Commissioner of Patents and Trademarks*